(12) United States Patent
Waki et al.

(10) Patent No.: US 8,734,351 B2
(45) Date of Patent: May 27, 2014

(54) METHOD OF DISPLAYING ELASTIC IMAGE AND DIAGNOSTIC ULTRASOUND SYSTEM

(75) Inventors: Koji Waki, Chiba (JP); Tsuyoshi Shiina, Ibaraki (JP); Makoto Yamakawa, Ibaraki (JP); Masaru Maeda, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 944 days.

(21) Appl. No.: 11/573,221

(22) PCT Filed: Aug. 4, 2005

(86) PCT No.: PCT/JP2005/014279
§ 371 (c)(1),
(2), (4) Date: Feb. 5, 2007

(87) PCT Pub. No.: WO2006/013916
PCT Pub. Date: Feb. 9, 2006

(65) Prior Publication Data
US 2008/0071174 A1 Mar. 20, 2008

(30) Foreign Application Priority Data
Aug. 5, 2004 (JP) ................................. 2004-229459

(51) Int. Cl.
*A61B 8/00* (2006.01)
*A61B 8/08* (2006.01)
*G01S 7/52* (2006.01)

(52) U.S. Cl.
CPC ............. *A61B 8/485* (2013.01); *G01S 7/52042* (2013.01)
USPC ....................................................... 600/442

(58) Field of Classification Search
USPC ................................................ 600/422, 442
See application file for complete search history.

(56) References Cited

U.S. PATENT DOCUMENTS 5,615,680 A * 4/1997 Sano .............................. 600/437
5,678,565 A * 10/1997 Sarvazyan .................... 600/587
(Continued)

FOREIGN PATENT DOCUMENTS

| EP | 1 541 089 | 6/2005 |
| JP | 61-244332 | 10/1986 |

(Continued)

OTHER PUBLICATIONS

"Real Time Tissue Elasticity Imaging Using The Combined Autocorrelation Method" Shiina et al, Journal of Medical Ultrasonics, Feb. 15, 1999, vol. 26, No. 2, pp. 57-66.

(Continued)

*Primary Examiner* — Tse Chen
*Assistant Examiner* — Hien Nguyen
(74) *Attorney, Agent, or Firm* — Antonelli, Terry, Stout & Kraus, LLP.

(57) ABSTRACT

A method of displaying an elastic image according to the present invention includes the steps of measuring ultrasound cross-section data of a cross-section region of a subject while applying compression to the subject 1 (2, 3, 4), determining distortion of tissue in the cross-section region on the basis of the ultrasound cross-section data, generating an elastic image of the cross-section region on the basis of the distortion, displaying the elastic image on a display device (7), setting a plurality of ROIs on the elastic image displayed on the display device, converting the distortion of each ROI into an index value (12), and displays the index value on the display device (8). In this way, the method enables quantitative evaluation of the hardness of body tissue of a region to be diagnosed.

20 Claims, 14 Drawing Sheets

(56) References Cited

U.S. PATENT DOCUMENTS

| | | | |
|---|---|---|---|
| 6,671,540 B1 * | 12/2003 | Hochman | 600/431 |
| 2002/0178833 A1 | 12/2002 | Chen | |
| 2005/0187470 A1 * | 8/2005 | Kubota et al. | 600/437 |

FOREIGN PATENT DOCUMENTS

| JP | 8-84729 | 4/1996 |
|---|---|---|
| JP | 2004-41617 | 2/2004 |
| WO | WO 2004/004574 | 1/2004 |
| WO | WO 2004/010872 | 2/2004 |

OTHER PUBLICATIONS

Office Action issued in European Patent Application No. 05 768 684.2 on Sep. 2, 2011.

Office Action issued in Chinese Patent Application No. 200580029684.7 on Jan. 22, 2010.

* cited by examiner

METHOD OF DISPLAYING ELASTIC IMAGE AND DIAGNOSTIC ULTRASOUND SYSTEM

TECHNICAL FIELD

The present invention relates to a method of displaying an elastic image and a diagnostic ultrasound system suitable for quantitatively evaluating the hardness (hereinafter referred to as "elasticity") of body tissue of a region to be diagnosed by ultrasound examination.

BACKGROUND ART

A diagnostic ultrasound system transmits ultrasonic waves to the inside of a subject by an ultrasound probe, receives a reflected echo signal of the ultrasonic waves corresponding to the structure of the body tissue from the inside of the subject, reconstructs a cross-sectional image, such as a B-mode image, and displays this for diagnosis.

Recently, it has been proposed to measure ultrasound image data by applying compression a subject by a manual or mechanical method, determine the displacement of various body regions caused by the compression on the basis of frame data of two ultrasound images having different measurement time periods, and generate an elastic image representing the elasticity of the body tissue on the basis of the displacement data. Various physical values correlating to the elasticity of body tissue are known, and, for example, distortion or an elasticity modulus of the body tissue is used. Here, distortion is a relative value obtained by spatially differentiating displacement, which is the amount of movement of the body tissue, and elasticity is a quantitative value obtained by dividing the change in stress acting on each body region by displacement.

For an elastic image, for example, as discussed in Patent Document 1, an elastic image colorized by adding color information, such as red, blue, and other colors, to regions in the tissue in accordance with the distortion or the elasticity modulus.

Since the displacement of the body tissue changes depending on the magnitude of the compression force, even for body tissue in the same region, distortion increases when strongly compressed. Therefore, a color elastic image representing distortion merely represents a relative display of the distortion of the regions on the color elastic image, and hardness cannot be quantitatively evaluated.

Patent Document 2 proposes to set two regions of interest (ROIs) in a B-mode image, measure the distortions in the two ROIs, and displaying numerical values of distortions in relation to the two ROIs on an image. Accordingly, by comparing the distortions of the two ROIs, the hardness of the ROIs can be relatively evaluated.

In other words, according to the technique described in Patent Document 2, the two ROIs may be set to a region that is presumed to be a tumor, such as cancer, and a region where no tumor exist, the distortions in the two ROIs are compared, and the distortion of the tumor is relatively evaluated with respect to that of the region without a tumor.

However, since a B-mode image does not represent distortion of tissue, it is difficult to recognize regions having different distortions. Thus, according to the technique described in Patent Document 2, it is difficult to appropriately set the magnitudes and the positions of the two ROIs whose distortions are to be compared.

Moreover, according to Patent Document 2, hardness cannot be quantitatively evaluated because consideration is not taken into account for a case in which, for example, the hardness of a region that is presumed to be an affected region, such as a tumor, be represented as an index, such as a ratio, with reference to a region of normal tissue or a region of body tissue having less individual difference in hardness.

Patent Document 1: JP2000-60853A
Patent Document 2: US2002/017883A1

DISCLOSURE OF INVENTION

An object of the present invention is to provide a method of displaying an elastic image and a diagnostic ultrasound system for quantitatively evaluating the hardness of body tissue in a region to be diagnosed.

A method of displaying an elastic image according to the present invention that is capable of solving the above-identified problems includes the steps of measuring ultrasound cross-section data of a cross-section region of a subject while applying compression to the subject; determining a physical value correlating to the elasticity of tissue in the cross-section region on the basis of the ultrasound cross-section data; generating and displaying an elastic image of the cross-section region on the basis of the physical value; setting a plurality of regions of interest in the displayed elastic image; and converting the physical value of each of the regions of interest into an index value and displaying the index value together with the elastic image.

According to the present invention, since a plurality of regions of interest (ROIs) whose physical values correlating to the elasticity of the tissue, i.e., distortions or the elasticity moduli, are to be compared are set on the elastic image, for example, regions having different distortions can be easily recognized, the size and the positions of the plurality of ROIs to be compared can be appropriately set. In particular, since the distortions of the plurality of regions of interest related to the comparison are mutually converted into index values and the index values are displayed on the display device, the difference in the hardness of the regions of interest can be quantitatively evaluated and a highly accurate diagnosis is possible. For example, a ROI set in a region of normal tissue or a region in body tissue with small individual difference in hardness is set as a reference to represent the hardness of the ROI set in a region presumed to be an affected area, such as a tumor, as an index.

As regions of interest, a first region of interest and a second region of interest set in a large region surrounding the first region of interest are set. The second region of interest does not include the first region of interest. Therefore, since regions of interest can be set separately for a malignant region (first region of interest) and a benign region (second region of interest), the malignant region can be compared with the benign region to carry out an accurate diagnosis. However, the present invention is not limited, and the first region of interest and the second region of interest can be set away from each other. In either case, the ratio of the physical values of the first region of interest and the second region of interest or the ratio of the average values of the physical values of the regions of interest can be used as an index value.

Furthermore, a scale for the physical value on the display device can be displayed, and display marks can be displayed at positions on the scale corresponding to the physical values of the first region of interest and the second region of interest. In this way, the difference in hardness of the tissue in the first and second regions of interest can be quantitatively confirmed on one view.

As the regions of interest, a first region of interest set in an affected area and second and third regions of interest being set away from each other in the lateral direction of the elastic image and sandwiching the first region of interest may be set. In such case, the index value may be a ratio of the physical value of the first region of interest and the sum of the physical values of the second and third regions of interest. In this way, even when the pressure applied to the regions of interest is biased, the average of an area where pressure is weak and an area where the pressure is strong may be obtained to balance the stress.

Furthermore, it is preferable for displaying a colored elastic image to determine average values of the physical values of the regions of interest and respectively relate the minimum value and the maximum value of the average values to a lower limit value and an upper limit value of a dynamic range of color information for color conversion. In this way, the resolution of the color display can be improved. In such a case, the level of the dynamic range corresponding to an intermediate value can be variably set when at least three regions of interest are set and the intermediate value is between the minimum value and the maximum value of the average values of the physical values. In this way, by changing the gradation between the regions of interest to increase the gradation, visual observation is facilitated.

The method of displaying an elastic image according to the present invention is not limited to comparing the hardness of tissue in a plurality of regions of interest in the same cross-section region. For, for example, tissue in corresponding regions, such as the left and right hands, feet, or breasts, the ultrasound cross-section data of each of left and right cross-section regions, which are symmetrical, of the subject are measured; elastic images of the left and right cross-section regions can be generated and displayed; two regions of interest can be set in each of the left and right displayed elastic images; the ratio of the physical values of the two set regions of interest can be determined for each of the left and right elastic images; and the ratio of the ratios of the physical values of the two regions of interest can be determined for the left and right elastic images. In this way, the difference in the hardness of the tissue in corresponding regions, such as the left and right hands, feet, or breasts, can be quantitatively evaluated, and the accuracy of the diagnosis can be improved.

The method of displaying an elastic image according to the present invention may include the steps of measuring the ultrasound cross-section data for a plurality of frames; determining the change over time of the physical value correlating to the elasticity of the tissue in the cross-section region on the basis of the plurality of frames of the ultrasound cross-section data; generating and displaying on a display device a moving image of an elastic image of the cross-section region on the basis of the change over time of the physical value; setting at least two regions of interest on a still image of the elastic image displayed on the display device; and displaying on the display device the change over time of the physical value of each of the regions of interest.

In this way, quantitative comparison of regions of interest for distortions that change in accordance with the change in the compression force can be accurately carried out. In such a case, the physical value of each of the regions of interest can be converted into an index value, and the change over time of the index value can be displayed on the display device. The change in the added value obtained by adding in order the index values of the regions of interest corresponding to a plurality of frames can be displayed on the display device. Furthermore, a time average of the index values of the regions of interest corresponding to a plurality of frames can be determined and displayed on the display device.

A diagnostic ultrasound system that carries out a method of displaying an elastic image according to the present invention may include ultrasound cross-section data measuring means for measuring ultrasound cross-section data of a cross-section region of a subject while applying compression to the subject with an ultrasound probe; signal processing means for processing the measured ultrasound cross-section data and generating a cross-sectional image; elastic-information computing means for determining a physical value correlating to the elasticity of tissue in the cross-section region on the basis of the measured ultrasound cross-section data and generating an elastic image of the cross-section region on the basis of the physical value; a display device for displaying the cross-sectional image and/or the elastic image; inputting means for setting a plurality of regions of interest in the elastic image displayed on the display device; and indexing means for converting the physical value of each of the set regions of interest into an index value and displaying the index value on the display device.

The diagnostic ultrasound system may include pressuring controlling means for supporting the ultrasound probe and for increasing or decreasing the compression applied to the subject with the ultrasound probe and fixing means for supporting the pressuring controlling means. In this way, since compression can be applied at constant pressure and constant speed to body tissue without depending on the repulsive force of the subject, a distortion elastic image with excellent reproducibility and evaluation ability can be obtained, and the index values of the physical values correlating to the elasticity according to the present invention can be stabilized.

BEST MODE FOR CARRYING OUT THE INVENTION

Embodiments of the present invention will be described below with reference to the accompanying drawings.

First Embodiment

Figure 1:
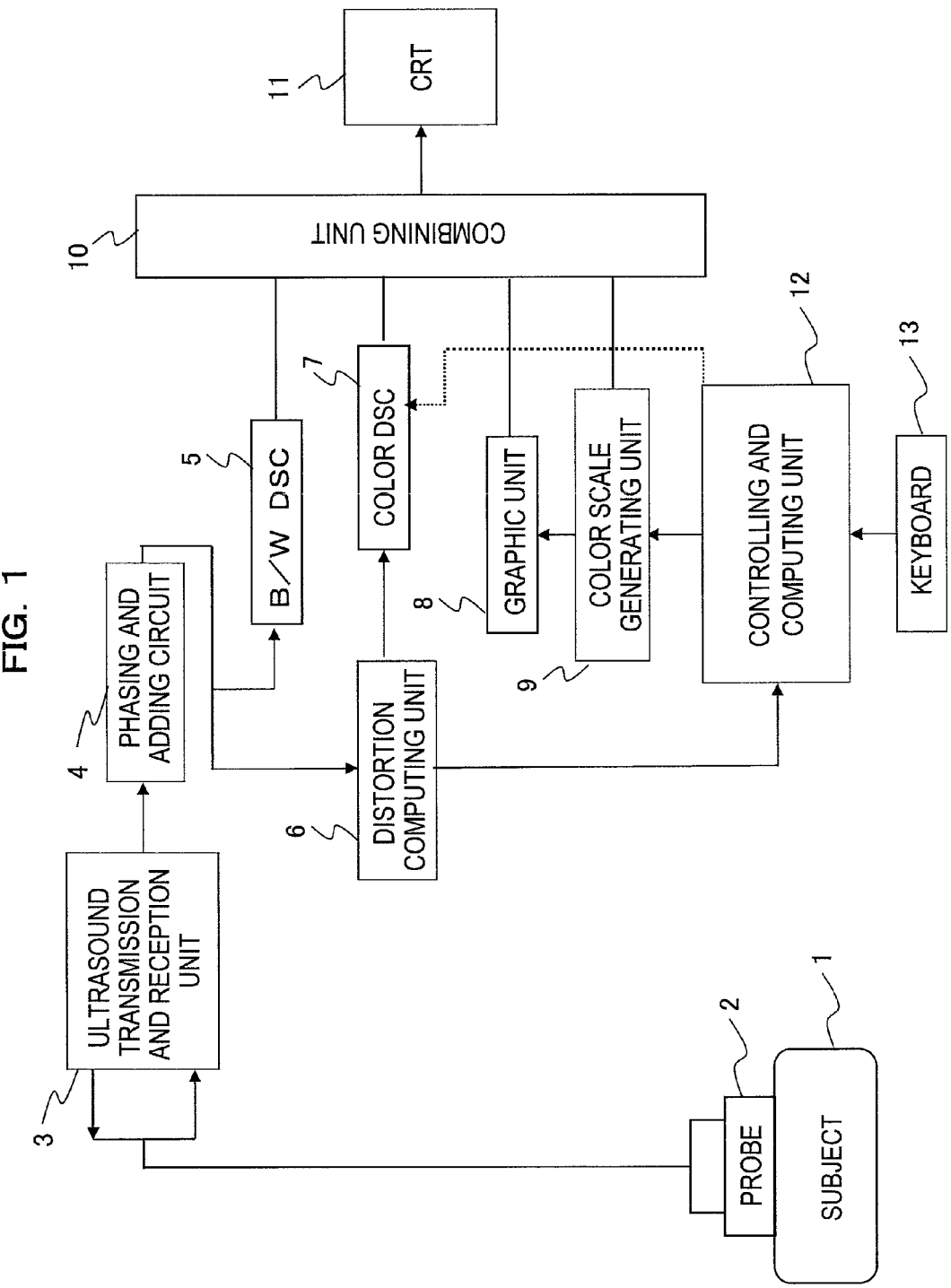
FIG. 1 illustrates the overall structure of a diagnostic ultrasound system according to an embodiment employing a method of displaying an elastic image according to the present invention.
Figure 2:
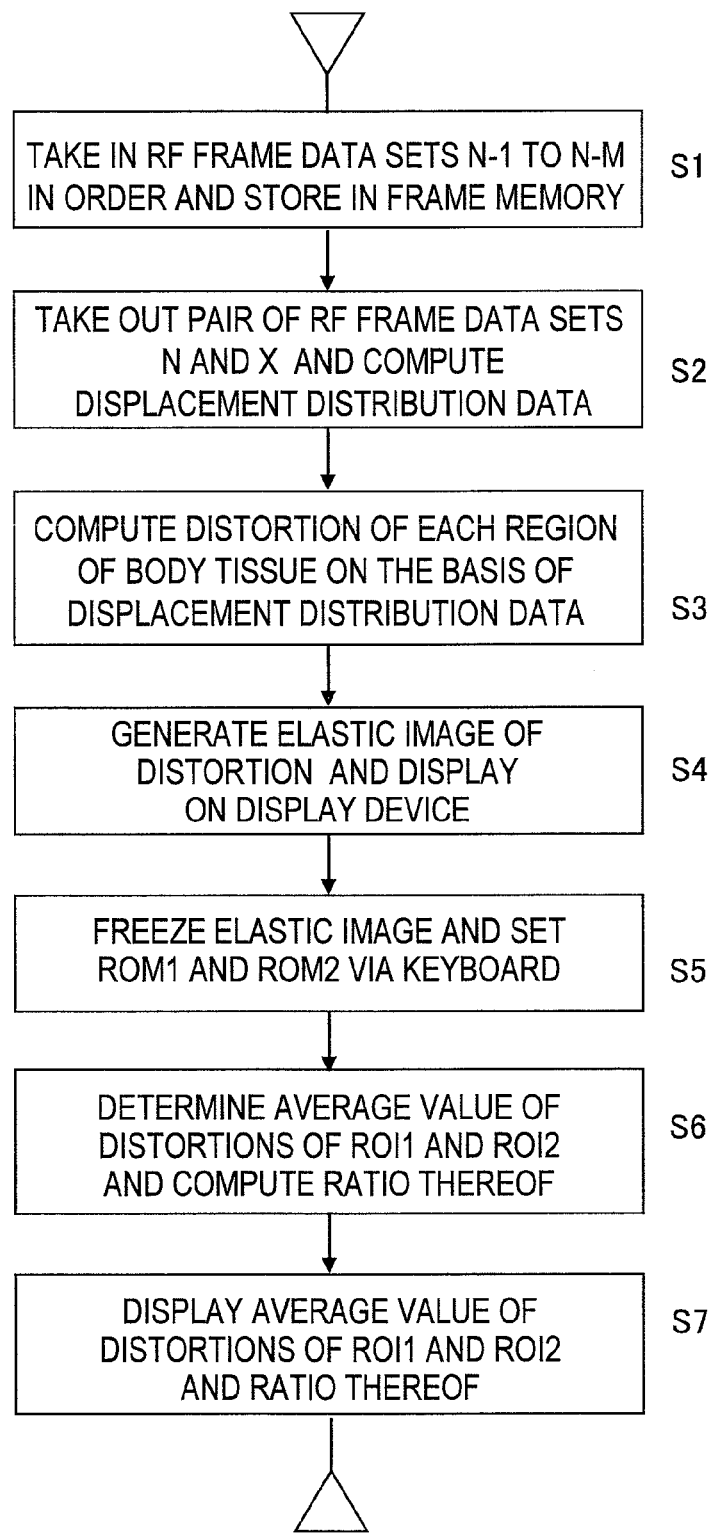
FIG. 2 is a flow chart illustrating an embodiment of the process according to the elastic image according to the present invention.

FIG. 1 illustrates the overall structure of a diagnostic ultrasound system according to an embodiment of the present invention. FIG. 2 illustrates a flow chart of a process of a method of displaying an elastic image according to an embodiment of the present invention. As shown in FIG. 1, the diagnostic ultrasound system according to this embodiment includes an ultrasound probe 2 used in contact with a subject 1, an ultrasound transmission and reception unit 3, a phasing and adding circuit 4, a cross-sectional-image configuring unit 5, a distortion computing unit 6, an elastic-image configuring unit 7, a graphic unit 8, a color-scale generating unit 9, an image combining unit 10, an image display unit 11, a controlling and computing unit 12, and a keyboard 13.

The probe 2 is constituted of a plurality of transducers and has a function of electrically carrying out electronic beam scanning on a predetermined cross-section region of the subject 1 and transmitting and receiving ultrasonic waves to and from the subject 1.

The ultrasound transmission and reception unit 3 repeatedly transmits ultrasonic waves in time intervals to the predetermined cross-section region of the subject 1 through the probe 2 and receives reflected echo signals from the cross-section region. In other words, when transmitting, the ultrasound transmission and reception unit 3 has a function of driving the probe to generate a transmission pulse for generating ultrasonic waves and setting a converging point of the transmitted ultrasonic waves at a predetermined depth. When receiving, the reflected echo signals received at the probe 2 are amplified by a predetermined gain and RF signals, i.e., reception signals, are generated.

The phasing and adding circuit 4 receives the amplified RF signals from the ultrasound transmission and reception unit 3, matches and adds the phases, and generates in time-sequence ultrasound cross-section data, which is RF signal data, converged at a plurality of converging points.

The probe 2, the ultrasound transmission and reception unit 3, and the phasing and adding circuit 4 constitutes ultrasound cross-section data measuring means for measuring ultrasound cross-section data of a cross-section region of the subject while applying compression to the subject 1 with the probe 2.

The cross-sectional-image configuring unit 5 constitutes signal processing means for generating a cross-sectional image by processing ultrasound cross-section data and reconfigures a dark and light cross-sectional image, such as a monochrome image, of a cross-section region of the subject 1 on the basis of the RF signal data output from the phasing and adding circuit 4. In other words, the cross-sectional-image configuring unit 5 includes a signal processing unit and a monochrome scan converter. The signal processing unit receives the RF signal data from the phasing and adding circuit 4 and carries out signal processing, such as gain correction, log compression, detection, outline enhancement, and filtering, to obtain cross-sectional image data. The monochrome scan converter includes an A/D converter for converting the cross-sectional image data from the signal processing unit into a digital signal, a frame memory for time-sequentially storing a plurality of converted cross-sectional image data sets, and a controller. The cross-sectional-image configuring unit 5 obtains the cross-section frame data of the inside of the subject 1 stored in the monochrome scan converter or the frame memory as one image and reads out the obtained cross-section frame data in television synchronization.

The distortion computing unit 6 measures displacement of the body tissue of the cross-section region of the subject 1 on the basis of the RF signal output from the phasing and adding circuit 4 so as to determine distortion, as described below. The elastic-image configuring unit 7 includes an elastic data processing unit and a color scan converter and reconfigures a color elastic image on the basis of the distortion determined at the distortion computing unit 6. In other words, the distortion computing unit 6 and the elastic-image configuring unit 7 constitute elastic-information computing means for determining distortion, which is a physical values correlating to the elasticity of tissue in the cross-section region, on the basis of the ultrasound cross-section data and for generating an elastic image of the cross-section region on the basis of the physical value.

The graphic unit 8 visualizes an image other than the ultrasound signal. The color-scale generating unit 9 generates a color scale of the distortion of an elastic image, as described below. The image combining unit 10 combines the monochrome cross-section image output from the cross-sectional-image configuring unit 5, the color elastic image output from the elastic-image configuring unit 7, a data image, such as the elastic data, output from the graphic unit 8, and a color scale output from the color-scale generating unit 9, at a specific address. The image display unit 11 displays the combined image generated at the image combining unit 10. The image combining unit 10 includes a frame memory, an image processing unit, and an image selecting unit and selects and combines the monochrome cross-section image, the color elastic image, the data image, and the color scale that are input in accordance with a command sent from the controlling and computing unit 12.

The controlling and computing unit 12 controls the above-described components in accordance with a process set in advance or in accordance with commands input accordingly through the keyboard 13. The keyboard 13 is an interface for various settings. In particular, the keyboard 13 according to this embodiment constitutes inputting means for setting a plurality of regions of interest on a still image of an elastic image displayed on the image display unit 11. The controlling and computing unit 12 includes indexing means for mutually converting the distortions of the regions of interest set in the elastic image into index values via the keyboard 13 and for displaying the index values on the image display unit 11 via the graphic unit 8.

Next, the detailed structure and the operation of the diagnostic ultrasound system according to this embodiment will be described with reference to the process shown in the flow chart in FIG. 2. Since the basic operation of the diagnostic ultrasound system is known, functions and operations related to the method of displaying an elastic image according to the present invention will be mainly described.

(Step S1)

The distortion computing unit 6 includes an RF signal selecting unit and a displacement computing unit and is provided in a diverging manner after the phasing and adding circuit 4. The RF signal selecting unit includes a frame memory and a selector. The RF signal selecting unit stores a plurality of RF signal data sets from the phasing and adding circuit 4 in the frame memory and selects one pair of RF signal frame data sets, i.e., two sets of RF signal frame data having different measurement time periods, from the stores RF signal frame data group using the selector.

For example, the RF signal selecting unit stores in order the RF signal data sets generated in time sequence on the basis of the frame rate of the images from the phasing and adding circuit 4 in the frame memory. Then, the selector selects the currently stored RF signal frame data set (N) as a first data set in accordance with a command from a controlling unit not shown in the drawings. At the same time, one RF signal frame data set (X) is selected from an RF signal frame data group (N-1, N-2, N-3, . . . N-M) stored in the past in terms of time. Here, the characters N, M, and X are index numbers added to the RF signal frame data and are positive integers.

(Step S2)

The displacement computing unit of the distortion computing unit 6 determines the displacement of body tissue from a pair of RF signal frame data sets. For example, the displacement computing unit carries out one-dimensional or two-dimensional correlation processing on the pair of RF signal frame data set (N) and RF signal frame data set (X) that has been selected by the RF signal selecting unit so as to determine a one-dimensional or two-dimensional displacement distribution related to a movement vector (direction and magnitude of displacement) representing the displacement of body tissue corresponding to each point on the cross-sectional image. Here, a block matching method is employed to detect the movement vector.

(Step S3)

The distortion is calculated by spatially differentiating the displacement, which is the amount of movement, of the body tissue determined in Step S2. More specifically, when $\Delta L$ is the displacement measured at the displacement computing unit, the distortion (S) can be determined by the expression $S=\Delta L/\Delta X$ since $\Delta L$ can be calculated by spatially differentiating $\Delta L$.

Here, the block matching method is a known method for carrying out processing for dividing an image into blocks constituted of, for example, N×N pixels, focusing attention on a block in a region of interest, finding a block that is most similar to the block on which attention is focused on, and determining a sample value by referring to the block and carrying out predictive coding or, in other words, by the difference.

In this embodiment, a case in which the distortion is determined as elastic information will be described as an example. However, the present invention is not limited, and, an elasticity modulus may be determined as elastic information. Since the elasticity modulus is calculated by dividing the change of pressure by the change of the amount of movement, the pressure (stress) applied to each region of the body tissue must be determined. More specifically, for example, when the displacement measured by the displacement computing unit is $\Delta L$ and pressure measured by a pressure measuring unit, not shown in the drawings, is $\Delta P$, Young's modulus Ym, which is an elasticity modulus, can be calculated by the expression $Ym=(\Delta P)/(\Delta L/L)$. Since the elasticity modulus of body tissue corresponding to each point on the cross-sectional image is determined from Young's modulus Ym, two-dimensional elastic data sets can be continuously obtained. Young's modulus is the ratio of the simple tensile stress applied to an object to the distortion generated parallel to the tension.

(Step S4)

The elastic data processing unit of the elastic-image configuring unit 7 stores the elastic frame data sets output in time sequence from the distortion computing unit 6 in the frame memory and carries out image processing on the stored frame data in accordance with a command of a controlling unit, not shown in the drawings. The color scan converter of the elastic-image configuring unit 7 converts the elastic frame data output from the elastic data processing unit into image data with color information. In other words, the color scan converter converts the elastic frame data into image data with red (R), green (G), and blue (B), which are the three primary colors of light. For example, elastic data with a high level of distortion is converted into a red color code, and, at the same time, elastic data with a low level of distortion is converted into a blue color code. The gradation of red (R), green (G), and blue (B) is 256, where, 255 represents display in high brightness and, in contrast, 0 represents no display at all. An operation units, such as the keyboard 13, is connected to the color scan converter via the controlling and computing unit 12. The control unit control the color of the elastic image. Furthermore, a pressure gauge (not shown in the drawings) may be provided on the probe 2 so as to provide a pressure measuring unit (not shown in the drawings) for measuring the pressure applied by pressing the probe 2 against the subject 1.

The combining unit 10 stores image data output from the cross-sectional-image configuring unit 5, the elastic-image configuring unit 7, and the graphic unit 8 in the frame memory. The image processing unit of the combining unit 10 adds and combines the cross-sectional image data and the elastic image data stored in the frame memory by a set percentage corresponding to a command from the controlling unit. Therefore, the brightness information and the color information of each pixel of the combined image are defined by adding the information sets for the monochrome cross-sectional image and the color elastic image by a set percentage. Moreover, the image selecting unit of the combining unit 10 selects an image to be displayed on the image display unit 11 from the cross-sectional image data and the elastic image data in the frame memory and the combined image data in the image processing unit, in accordance with a command form the controlling unit and displays the image on the image display unit 11.

(Step S5)

Figure 3:
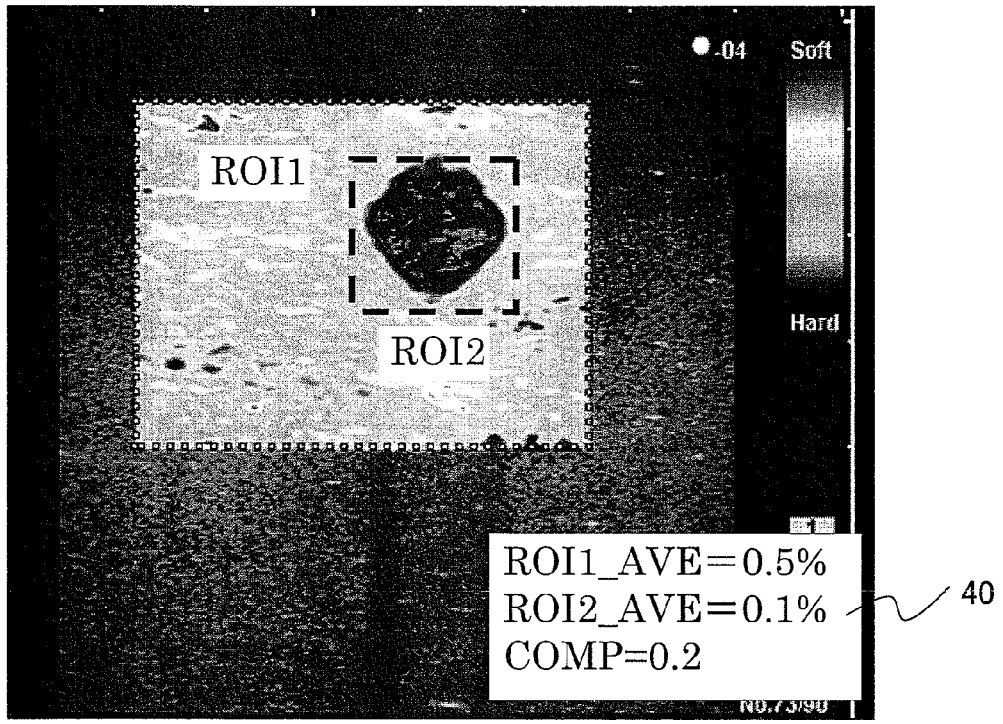
FIG. 3 illustrates a display example of an elastic image.

An elastic image is displayed on the image display unit 11 by inputting a command is from the keyboard 13, and, at the same time, the displayed elastic image is frozen at a given timing to set, for examples, two regions of interest $ROI_1$ and $ROI_2$ whose elasticity values are to be compared, as shown in FIG. 3. For example, the $ROI_1$ is set in a large region surrounding the $ROI_2$. In other words, the $ROI_2$ is set in a region that has small distortion (hard) that is presumed to be affected, such as a tumor, in the elastic image. Then, the $ROI_1$, which is a reference for the index, is set in a region that is presumed to be a normal region in the elastic image and that is a large region surrounding the $ROI_2$ so as to be compared with the distortion of the $ROI_2$. Here, the $ROI_2$ is the region that does not include the $ROI_1$. The controlling and computing unit 12 outputs a command to the graphic unit 8 for displaying the $ROI_1$ and $ROI_2$ whose setting are input from the keyboard 13 in white dotted lines, as shown in FIG. 3. The image for setting the ROIs can be a combined image obtained by superimposing a color elastic image on a monochrome B-mode image. In FIG. 3, the image is monochrome. However, the actual image is colored in red, blue, and other colors, so that the spreading and size of the affected region, such as a tumor, can be easily diagnosed.

(Step S6)

Figure 4:
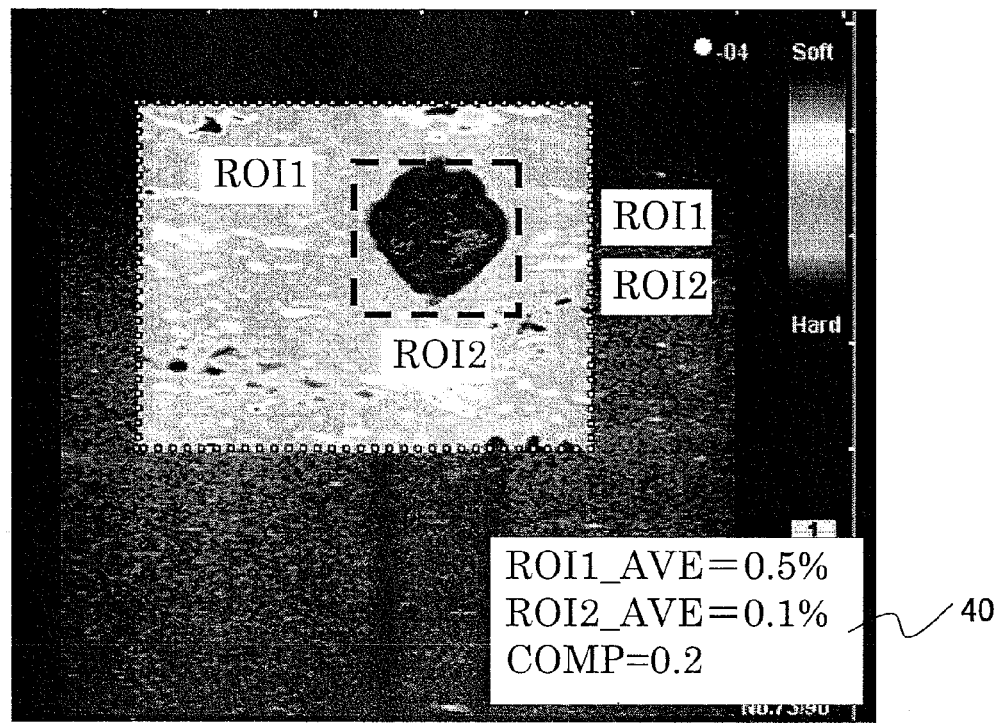
FIG. 4 illustrates another display example of an elastic image.
Figure 5:
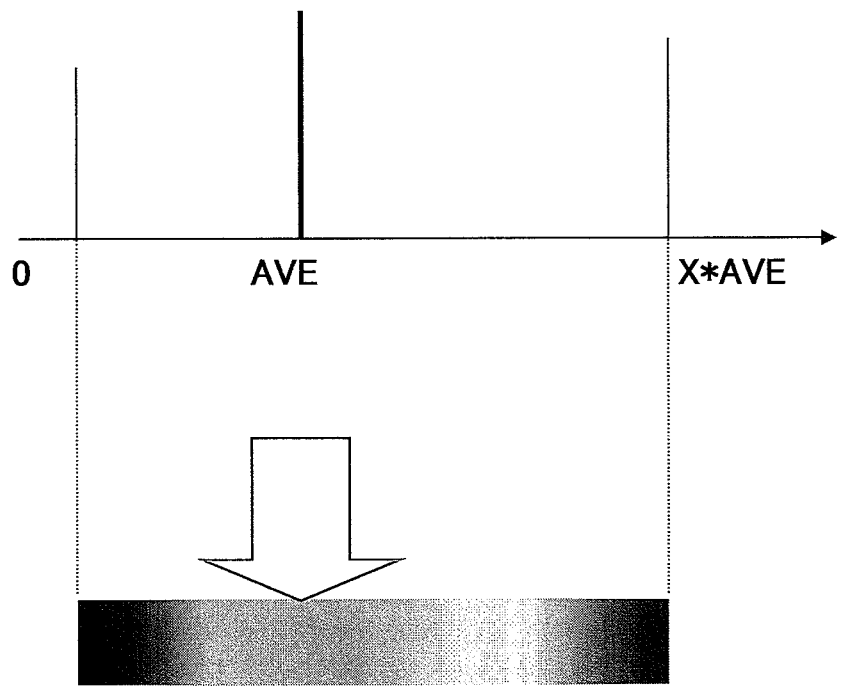
FIG. 5 illustrates a display example of a color scale in the example of the displayed image in FIG. 4.

The controlling and computing unit 12 calculates the distortions of the $ROI_1$ and $ROI_2$ set in the elastic image in FIG. 3 and includes the indexing means for calculating the distortion average values $ROI_1\_AVE$ and $ROI_2\_AVE$. The controlling and computing unit 12 calculates the distortion average value AVE per unit time by dividing the distortion by the time elapsed between the frames of the pair of RF signal frame data sets (N) and (X) related to distortion calculation and transfers the result to the graphic unit 8 so as to display a color scale representing the relationship of colors and magnitude of the distortion on a screen. At this time, the positions of the average values that are the reference for color scan conversion are indicated by arrows provided on or next to the color scale, as shown in FIG. 4. As shown in FIG. 5, the upper limit of the color value is X times the distortion average value AVE. Everything below the upper limit is linearly color scan converted to configure the color scale.

Next, the controlling and computing unit 12 calculates a distortion ratio COMP from the distortion average values $ROI_1\_AVE$ and $ROI_2\_AVE$. More specifically, the distortion ratio COMP is the ratio of the distortion average values of the $ROI_1$ and $ROI_2$, which are physical values (hardness) correlating to the elasticity of the tissue, and is an index value obtained by mutually converting the $ROI_1\_AVE$ and $ROI_2\_AVE$.

(Step S7)

Next, the controlling and computing unit 12 transfers the computation result to the graphic unit 8, displays a display window 40 in the lower right area of the screen as shown in FIGS. 3 and 4, and displays the distortion average values and the distortion ratio in the display window 40. In other words, $ROI_1\_AVE=0.5\%$, $ROI_2\_AVE=0.1\%$, and COMP=0.2 are displayed in the display window 40.

Here, the regions of interest $ROI_1$ and $ROI_2$ are independent regions of interest. When these regions overlap each other as shown in FIG. 3, the distortions and the average values can be calculated by removing the area of $ROI_2$ from the area of $ROI_1$.

As described above, the $ROI_2$ is set in a region that has small distortion (hard) that is presumed to be affected, such as a tumor, in the elastic image. However, the color scale may be used as a reference to automatically set the $ROI_2$. An arrow 41 may be set on the color scale, and the colors on the harder side of the set arrow 41 may be detected. The region corresponding to the detected colors is set as the $ROI_2$. In this way, the $ROI_2$ can be efficiently set by using the property that a tumorous region is a hard region.

As described above, according to this embodiment, since the distortion ratio (hardness ratio) of $ROI_1$ and $ROI_2$ is calculated and displayed on a screen, the hardness of an affected region can be quantitatively examined by comparing the hardness of the regions of interest. For example, since cancer is known to have a distortion ratio that is 10 times or more greater than that of fat, by setting the $ROI_1$ in a fat layer and the $ROI_2$ in a region that is presumed to be an affected region, such as cancer, and calculating the ratio, a method of accurately diagnosing cancer can be established. Furthermore, the $ROI_1$ can be automatically set in a region where fat exist relatively stably, such as a region at constant depth of 2 to 3 cm from the body surface.

As shown in FIG. 4, by displaying indicator marks, such as arrows, at positions corresponding to the average values of the distortion in the $ROI_1$ and the $ROI_2$ next to or on the color scale, the correlation of the distortions of the $ROI_1$ and $ROI_2$ can be recognized visually, instead of numerically. In other words, the relationship of the magnitude and the colors of the average value of the distortion in the $ROI_2$ can be grasped in detail.

When the $ROI_2$ is set as a point, the level of distortion at the point is displayed on the screen. Therefore, since an arrow is displayed at a position on the color scale corresponding to the magnitude of the distortion and the color, the user can grasp the distortion in more details.

Second Embodiment

In the above-described embodiment, a case in which two ROIs whose values of hardness ratio are to be compared are set is described. However, the present invention is not limited, and any number of ROIs to be used for comparison can be generated by the controlling and computing unit 12 and the keyboard 13. In such a case, the distortions of a plurality of ROIs can be mutually converted into index values.

Figure 6:
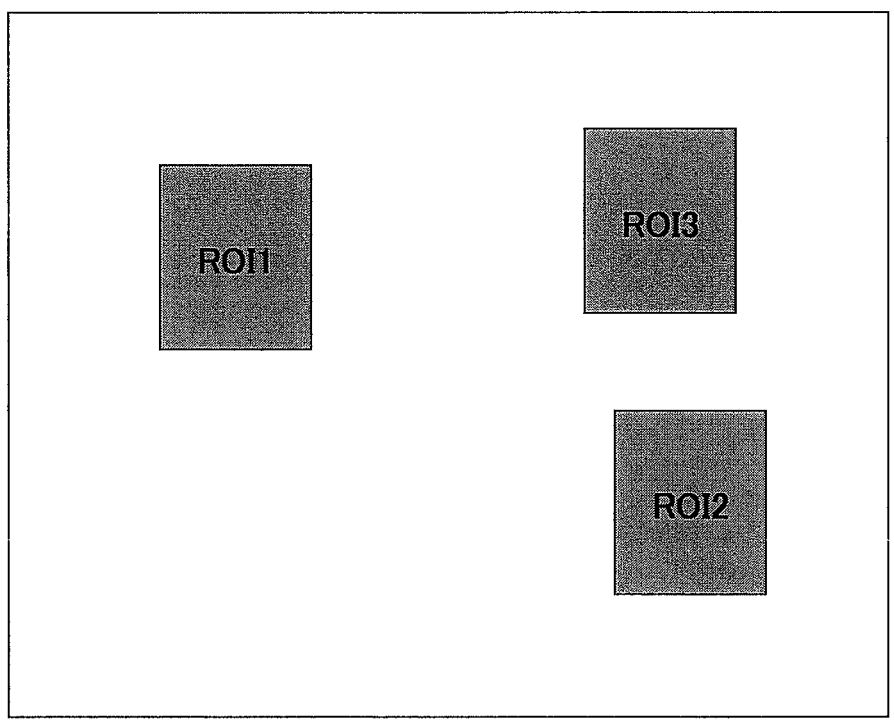
FIG. 6 illustrates another example of a method of setting a ROI.

A case in which three ROIs are set will be described with reference to FIG. 6. As shown in the drawing, on an elastic image or a combined image of an elastic image and a B-mode image, a $ROI_1$ is set, and $ROI_2$ and $ROI_3$, which are vertically provided at positions laterally apart from the $ROI_1$, are set. The distortions in these ROIs or the average values are mutually converted into index values, and the index values are displayed on the image display unit 11.

Examples of the index values for such a case are listed below.

(1) Ratio of distortion average values of ROIs

Ratio(1)=$ROI_1\_AVE/ROI_3\_AVE$

Figure 7:
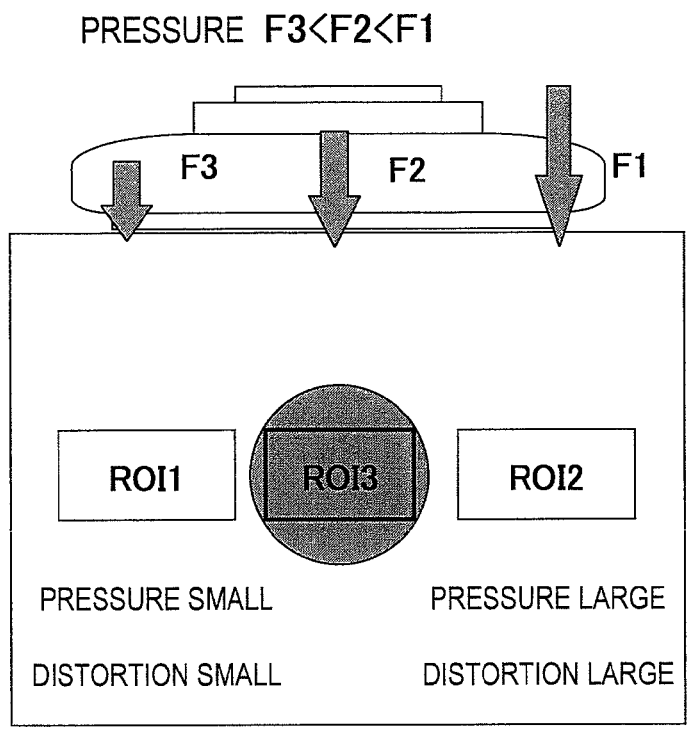
FIG. 7 illustrates another example of a method of setting a ROI.

Ratio(2)=$ROI_2\_AVE/ROI_3\_AVE$ (2) Ratio of the added values of distortions of ROIs Ratio(3)=$\Sigma ROI_1/\Sigma ROI_3$ Ratio(4)=$\Sigma ROI_2/\Sigma ROI_3$ (3) Ratio of a combination of a plurality of ROIs Ratio(5)=$(ROI_1+ROI_2)/ROI_3$ Here, an example of converting the ratio of a combination of a plurality of ROIs into an index values will be described with reference to FIG. 7. FIG. 7 schematically illustrates the relationship between the probe 2 for applying compression and an elastic image. In other words, $ROI_1$, $ROI_2$, and $ROI_3$ are set apart from each other in the lateral direction of the image in correspondence to the extending range of the probe 2, and the $ROI_3$ in the middle is set as a region presumed to be affected.

When compression is applied manually with the probe 2, compression forces F1 to F3 applied in the longitudinal direction of the probe 2 may not be uniform, as shown in FIG. 7. When there is a difference in the magnitudes of the compression forces, the values of distortion will be different even when the hardness of the body tissue is the same. Therefore, for example, even when the tissue of the $ROI_1$ and the tissue of $ROI_2$ are the same, the ratio of $ROI_1/ROI_3$ and the ratio of $ROI_2/ROI_3$ will be different values. Thus, as in the above-mentioned (3), by setting Ratio (5)=$(ROI_1+ROI_2)/ROI_3$ as an index, the differences in the magnitudes of the compression forces F1 and F3 can be compensated for.

Third Embodiment

Figure 8A:
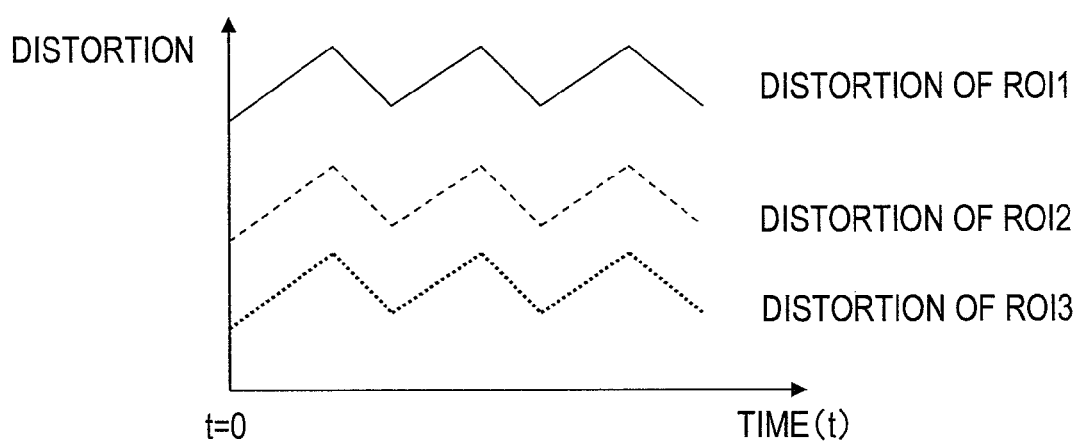
FIG. 8A illustrates a display example of change over time in distortion of each ROI.
Figure 8B:
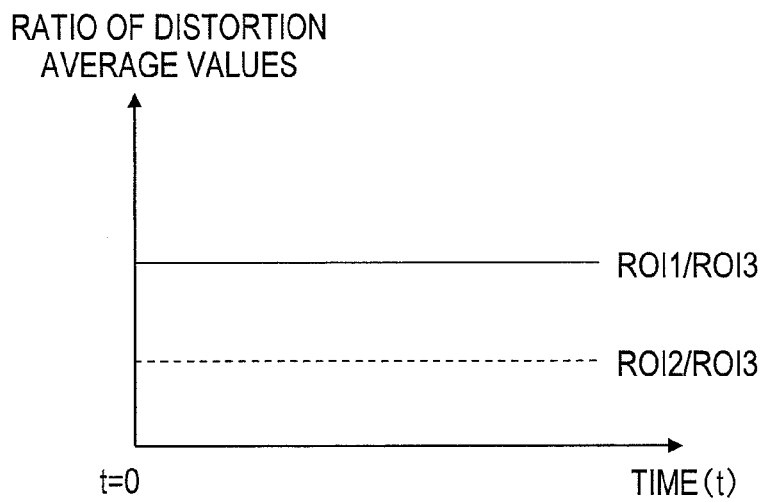
FIG. 8B illustrates a display example of change over time in the distortion ratio of each ROI.

In the above-described first and second embodiments, examples of converting the distortions of a plurality of ROIs to be compared into index values and displaying these on the image display unit 11 are described. However, the present invention is not limited, and, as shown in FIG. 8A or BB, the change over time of the distortions or the distortion ratios of $ROI_1$, $ROI_2$, and $ROI_3$ can be represented as a graph. The positions of the ROIs according to this embodiment are the same as those in FIG. 6.

More specifically, as shown in FIG. 8A or BB, by determining the distortions or the distortion ratios on the basis of ultrasound measurement data for a plurality of frames measured in time sequence and displaying the change over time as a graph, the difference in the hardness of the ROIs can be recognized without flaw.

FIG. 5B will be described in detail. Here, for the sake of description, the $ROI_1$ and $ROI_3$ are normal regions and the $ROI_2$ is a tumorous region. Since $ROI_1/ROI_3$ is the ratio of normal regions, the ratio of the distortion average values is substantially one. Since the distortion of the tumorous region is small compared with the distortion of the normal regions, the ratio of the distortion average values $ROI_2/ROI_3$ is a value smaller than one. In this way, by setting in advance the $ROI_3$, which is a normal region, and comparing each region with the $ROI_3$, it can be determined whether each region is a normal region or a tumorous region. The settings of the regions to be determined can be freely set with the keyboard 13. When a ROI is set, whether it is a normal region or a tumorous region is determined on the basis of the ratio of the distortion average values based on the $ROI_3$ at the controlling and computing unit 12. The determination result is displayed on the screen as characters or by displaying the inside of the ROIs in color. For color display, for example, a region is displayed in green when the region is determined to be a normal region (when the ratio is substantially one), whereas a region is displayed in orange when the region is to be determined to be a tumorous region (when the ratio is smaller than one). In other words, the controlling and computing unit 12 includes determining means for determining whether or not the tissue in each ROI is normal on the basis of the mutual ratios of the distortion average values of the ROIs and for displaying the determination results.

In theory, the distortion ratios will be constant values over time. If the distortion ratios change over time, erroneous compression is occurring. Thus, the operator can be encouraged to carry out the compression one more time.

Figure 8C:
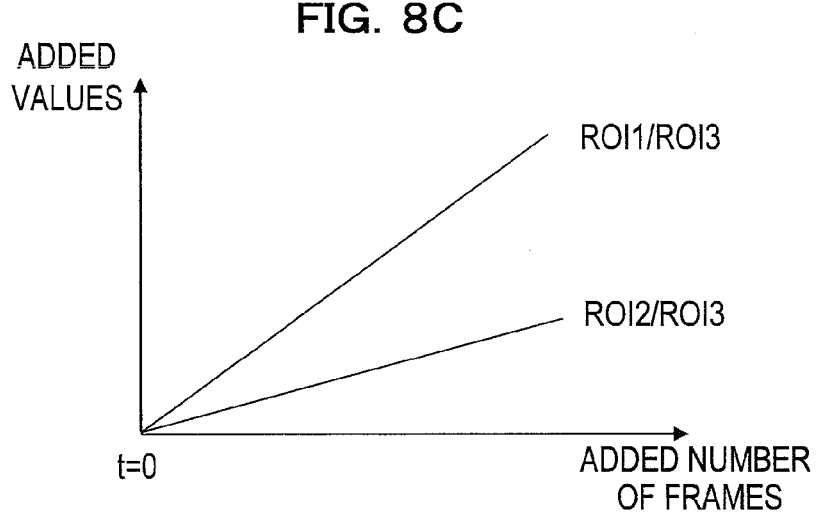
FIG. 8C illustrates a display example of change over time in distortion between the ROIs.

As shown in FIG. 8C, by adding the distortion ratios determined for the frames and displaying the added values corresponding to the added numbers of frames as a graph, the difference between the ratios of $ROI_1/ROI_3$ and $ROI_2/ROI_3$ will become clear.

More specifically, according to this embodiment, ultrasound cross-section data of a cross-section region is measured for a plurality of frames while applying compression to the subject 1, and the change over time of the distortion, which is a physical value correlating to the elasticity of tissue in the cross-section region, is determined on the basis of the ultrasound cross-section data for the plurality of frames. Then, a moving image of the elastic image for the cross-section region is generated on the basis of the change over time of the distortion and is displayed on a display device; at least two ROIs are displayed on a static image of the displayed elastic image; and the change over time of the distortion of each ROI is displayed. In this way, the distortions that change in accordance with the change in the compression force can be accurately and quantitatively compared for the ROIs.

Figure 9A:
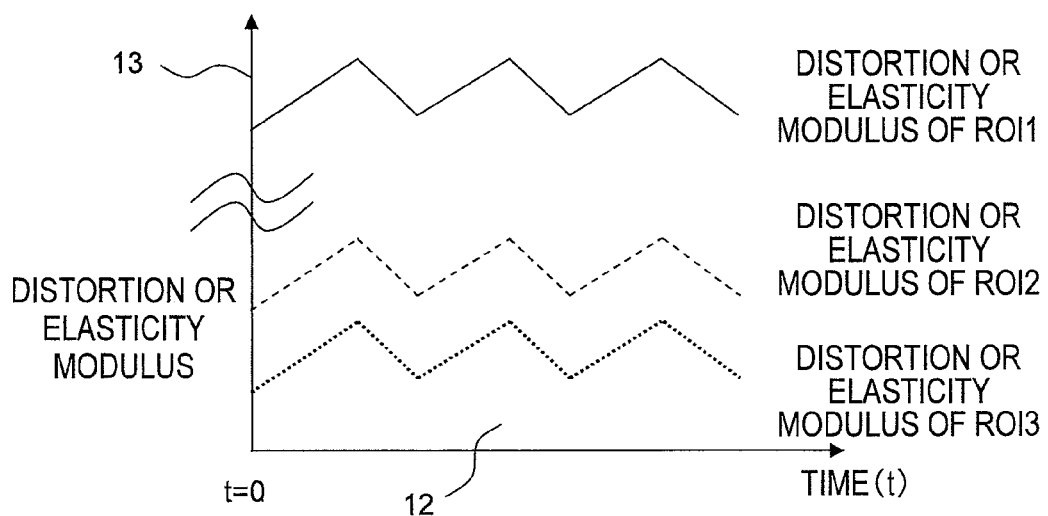
FIG. 9A illustrates a display example of change over time in distortion or elasticity modulus of each ROI.

FIG. 9A illustrates a configuration in which the display width is automatically adjusted by omitting the display of the distortion or the elasticity modulus between the $ROI_1$ and the $ROI_2$ on the display axis of the distortion or the elasticity modulus of the distortion graph since the distortion of $ROI_1$ is quite different from the distortions of the $ROI_2$ and $ROI_3$. According to this configuration, the distortions or the elasticity moduli for comparing a normal region and a tumorous region can be displayed in one screen.

Figure 9B:
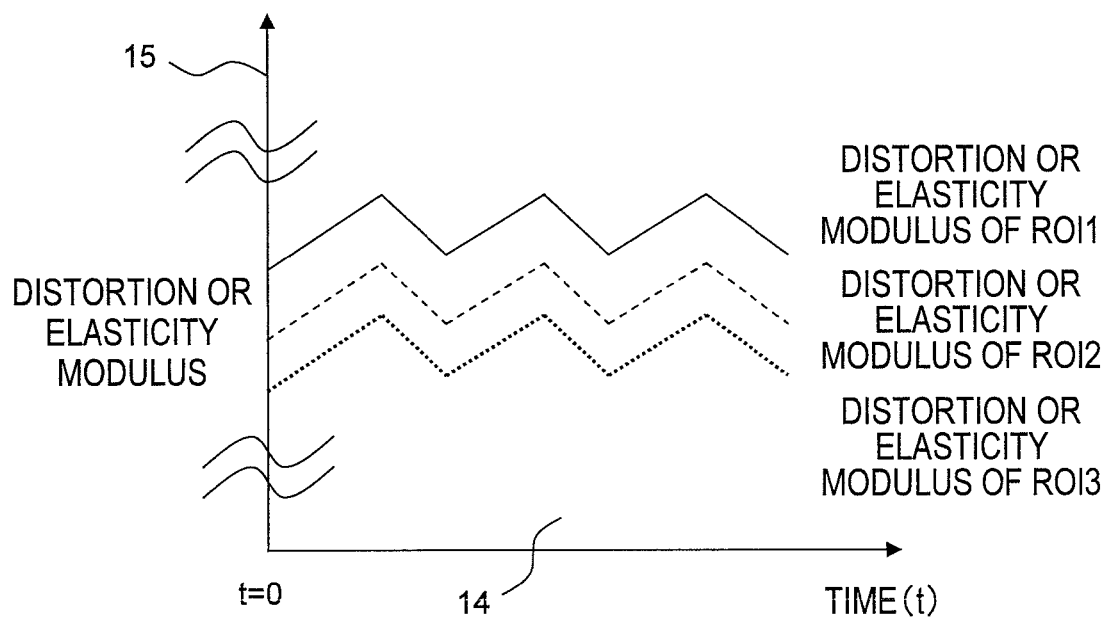
FIG. 9B illustrates another display example of change over time in distortion or elasticity modulus of each ROI.

FIG. 9B is a configuration in which the display width is automatically adjusted by omitting the upper and lower displays of the distortion on the display axis of the distortion or the elasticity modulus of the distortion graph since the distortions of all ROIs are concentrated in the central area. According to this configuration, the comparison range can be extended so that the distortions or the elasticity moduli are displayed in one screen.

Figure 10:
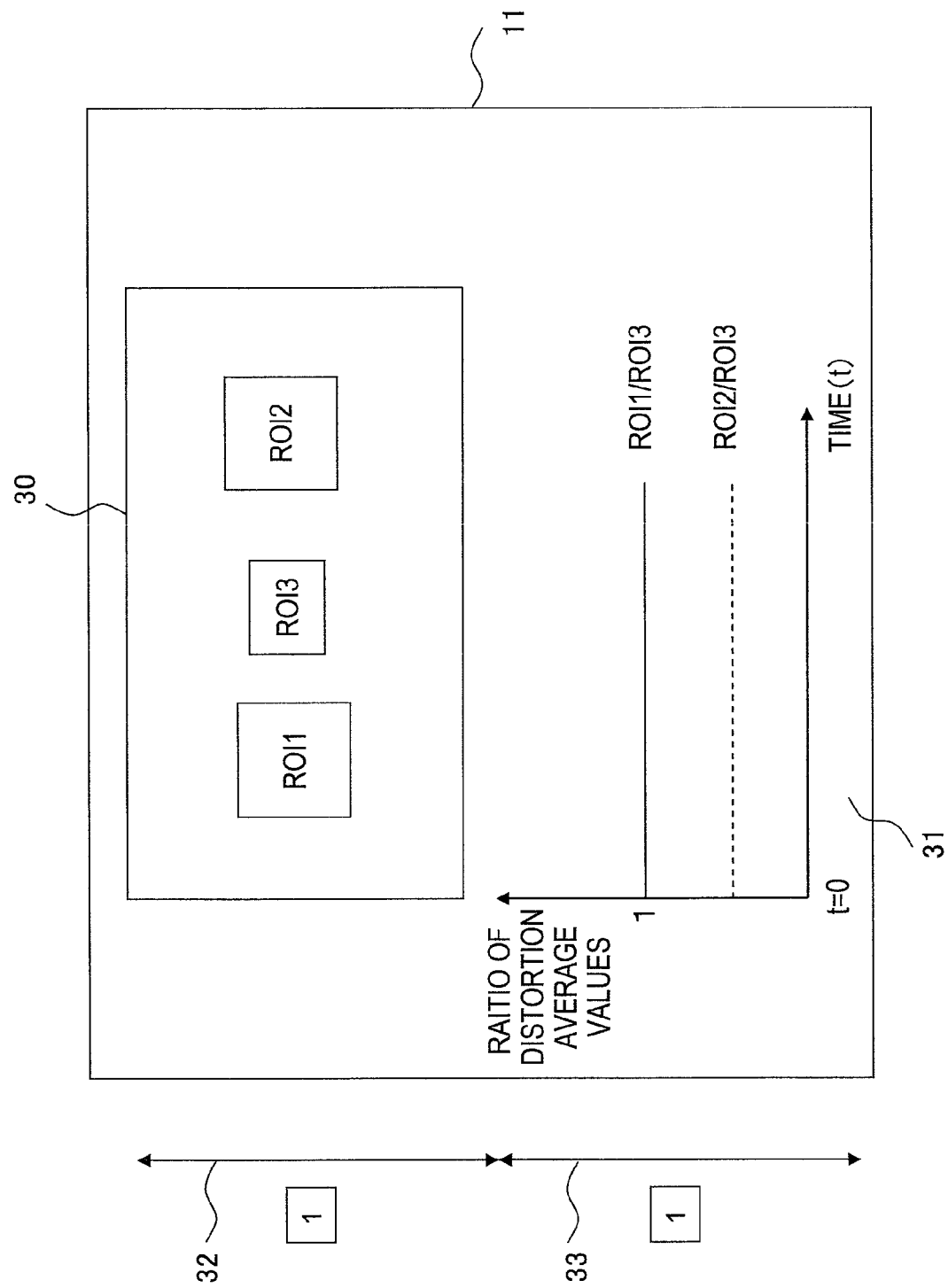
FIG. 10 illustrates a configuration for displaying an elastic image and a graph of the ratio of distortion average values fitting the ROIs.

FIG. 10 illustrates a configuration in which an elastic image 30 and a graph 31 of the ratios of the distortion average values corresponding to the ROIs are displayed on the same screen on the image display unit 11. The elastic image 30 is displayed in the upper area of the screen, and the graph 31 is displayed in the lower area of the screen. Accordingly, the ratios of the average values of the distortion corresponding to the ROIs can be relatively recognized in relation to the elastic image 30, and the elastic image can be observed while confirming the values of the ratios in time sequence. A width-adjustment arrow 32 is for adjusting the vertical distance of the elastic image 30. When the width of the width-adjustment arrow is decreased, the elastic image 30 shrinks. In contrast, when the width of the width-adjustment arrow is increased, the elastic image 30 is enlarged. More specifically, the distortion computing unit 6, which is elastic-information computing means, generates a plurality of elastic images based on a plurality of ultrasound cross-section data sets measured in time sequence, displays the generated elastic images and the cross-section image displayed on the image display unit 11 in an overlapping manner on the same screen, and also displays the change in the ratios of the average values of the distortions in the ROIs on the same screen.

Figure 11:
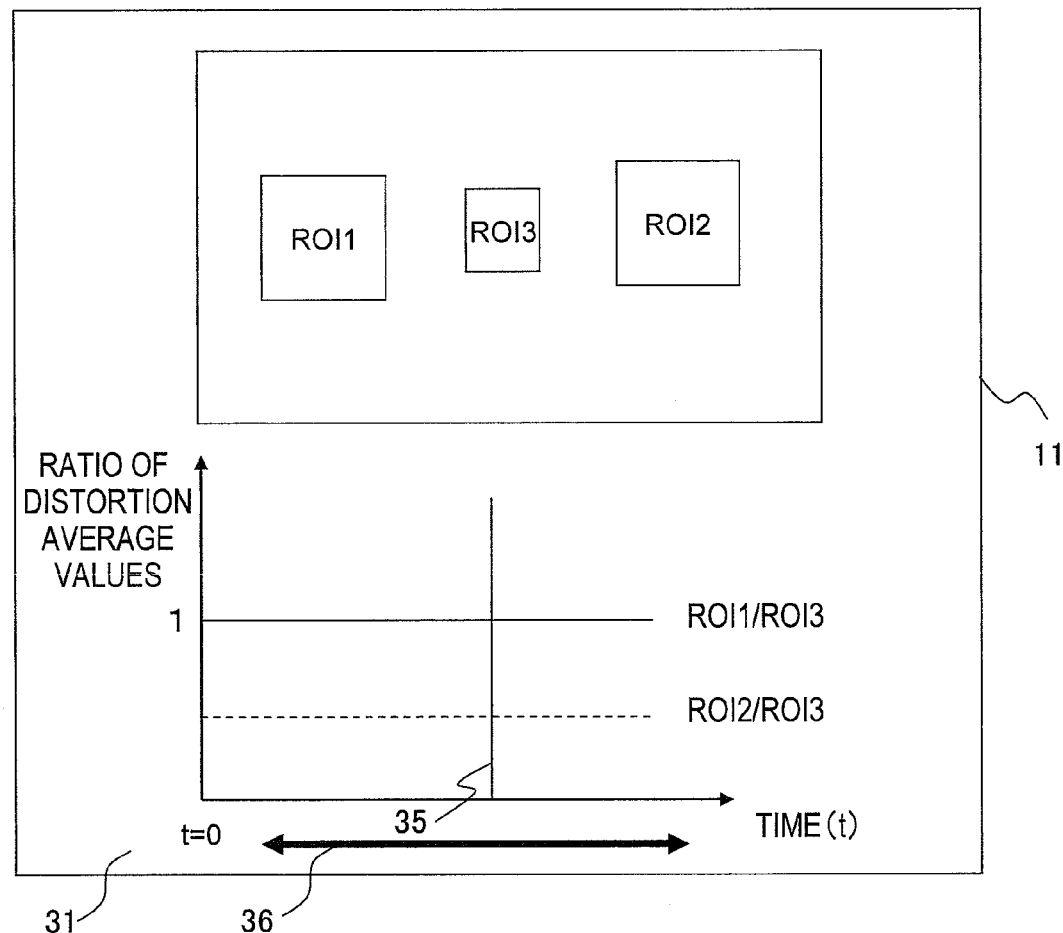
FIG. 11 illustrates a modification of the display configuration in FIG. 10.

FIG. 11 illustrates a configuration in which, in addition to the configuration shown in FIG. 10, a time phase bar 35 is displayed on the graph 31 of the ratios of the distortion average values and an elastic image 30 corresponding to the time phase bar 35 is displayed. Moreover, FIG. 11 illustrates a configuration for enabling loop playback in predetermined intervals. By moving the time phase bar 35 in the lateral direction with the keyboard 13, the controlling and computing unit 12 displays the elastic image 30 corresponding to a predetermined time phase. For example, on the basis of the graph of the ratios of the distortion average values of the ROIs, a time phase for optimal compression can be found from the slope, the maximum point, or the minimum point of the graph, and an elastic image 30 that corresponds to the time phase for optimal compression can be displayed. More specifically, when the distortion computing unit 6, which is the elastic-information computing means, generates a plurality of elastic images on the basis of a plurality of ultrasound cross-section data sets measured in time sequence and displays an elastic image corresponding to an assigned measurement time phase on the image display unit 11 when the time phase bar 35 for assigning the measurement time phase for the plurality of elastic images measured in time sequence is operated by the inputting means.

Furthermore, a start frame and an end frame for a predetermined interval are assigned; the display of the time axis is enlarged; and loop playback is carried out. An arrow 36 is a symbol indicating the start frame and the end frame. When all frames cannot be displayed on the time axis, the time axis is scrolled by the time phase bar 35.

Fourth Embodiment

The characteristics of another embodiment of a method of displaying an elastic image according to the present invention will be described with reference to FIGS. 12A to 12C. By variably setting a dynamic range in accordance with index values when the index values that relate to distortions and that are determined in the first to third embodiments are displayed in color, the resolution of the display in color can be improved.

Figure 12A:
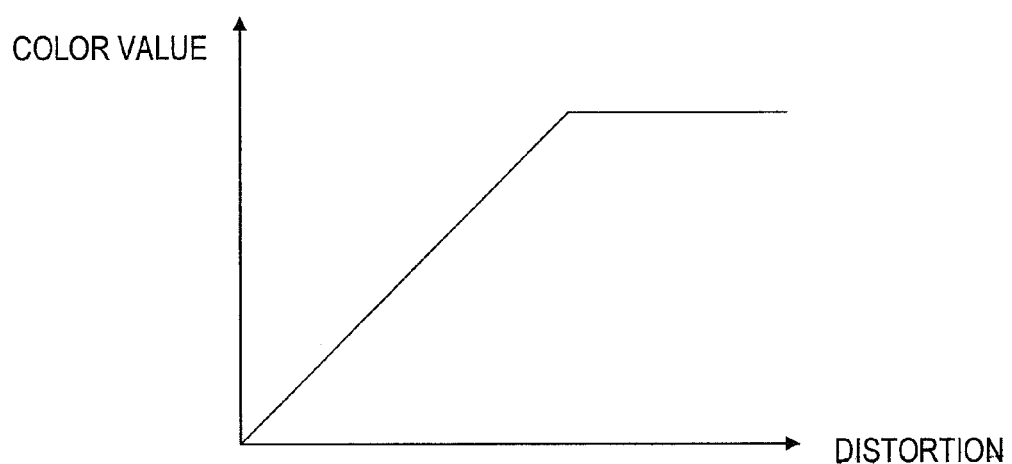
FIG. 12A illustrates an example setting of a typical dynamic range.
Figure 12B:
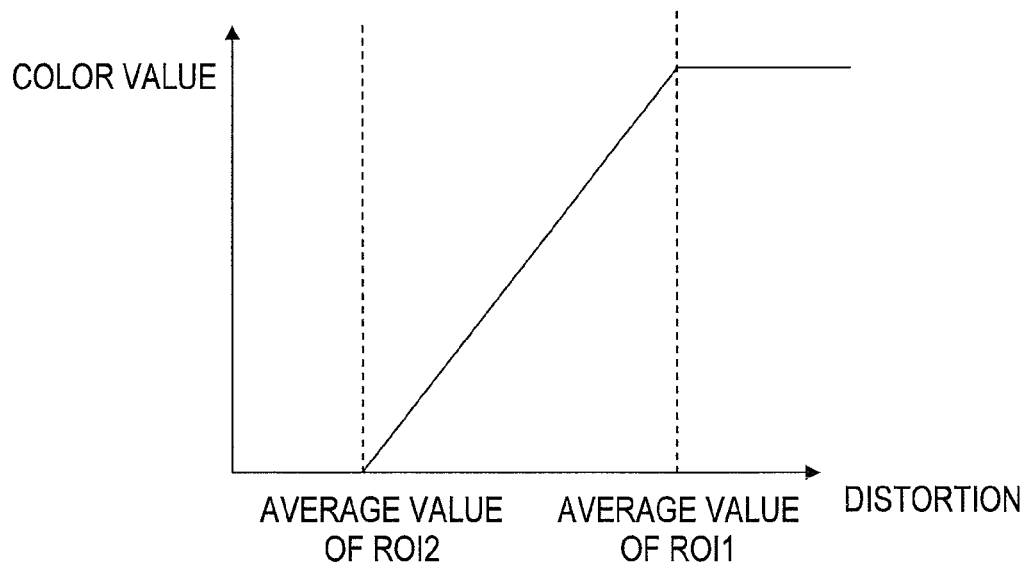
FIG. 12B illustrates an embodiment of an example setting of a typical dynamic range according to the present invention.
Figure 12C:
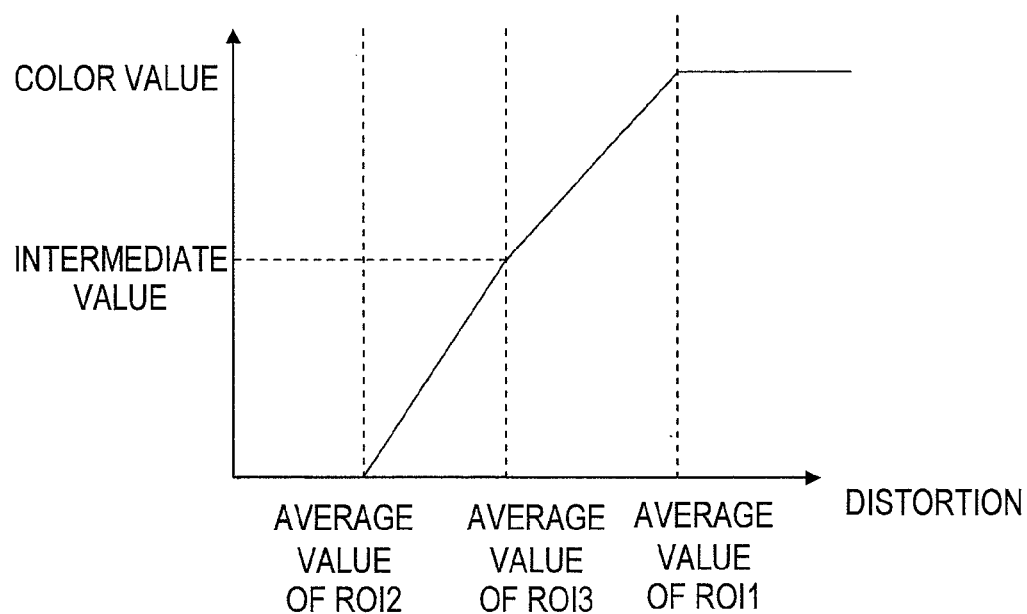
FIG. 12C illustrates another embodiment of an example setting of a typical dynamic range according to the present invention.

In other words, for a conventional dynamic range, as shown in FIG. 12A, color values are linearly assigned to the entire range of theoretical values of distortion. In contrast, according to this embodiment, for example, when two ROIs, $ROI_1$ and $ROI_2$, are set as shown in FIG. 3, the small value and the large value of the average values of distortions for the ROIs are related to the upper limit value and the lower limit value of the dynamic range of the color information for displaying in color, as shown in FIG. 12B. In this way, the resolution of the display in color can be improved. Furthermore, when three ROIs, $ROI_1$ $ROI_2$, and $ROI_3$, are set, as shown in FIG. 6, the minimum value and the maximum value of the average values of distortions of the ROIs are related to the upper limit value and the lower limit value of the dynamic range, as shown in FIG. 12C. Then, for example, by setting the color value to an appropriate level and setting a non-linear dynamic range for $ROI_3$ whose average value of distortion is an intermediate value, the resolution of the display in color for the target region can be improved.

Fifth Embodiment

The characteristics of another embodiment of a method of displaying an elastic image according to the present invention will be described with reference to FIG. 13. According to the above-described first to fourth embodiments, the hardness of the tissue of a plurality of ROIs in the same cross-section region is compared. However, the present invention is not limited and can be employed, for example, for diagnosing abnormal regions by separately measuring ultrasound cross-section data sets for left and right cross-section regions, which are symmetrical, such as the left and right hands, feet, or breasts of the subject, generating elastic images for the left and right cross-section regions, and comparing the elastic images.

Figure 13:
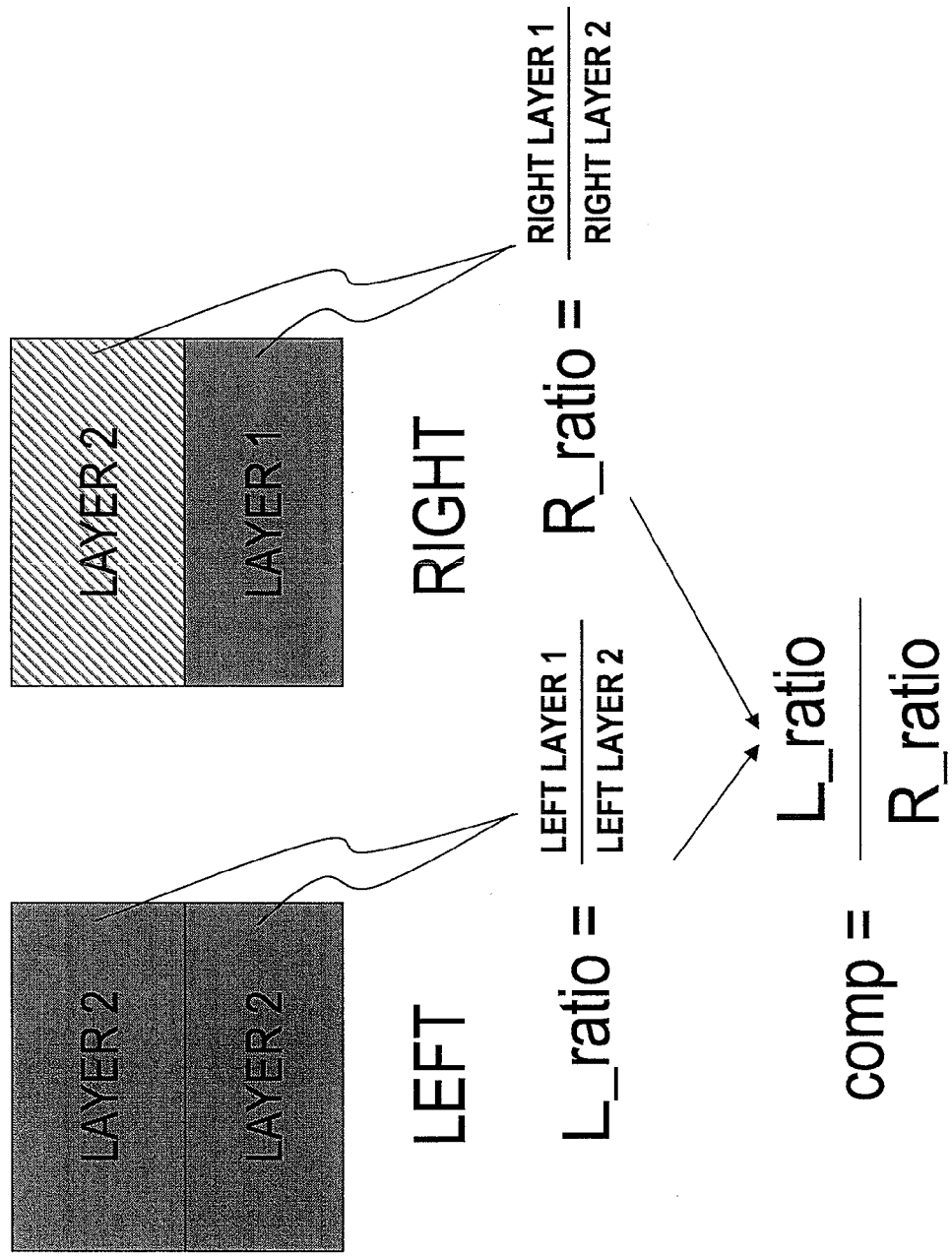
FIG. 13 illustrates the characteristics of another embodiment of the method of displaying an elastic image according to the present invention.

In other words, as shown in FIG. 13, two layers, layer 1 and layer 2, are set as regions of interest (ROIs) in each of the left and right elastic images. The ratios of the distortions of the layers 1 and the layers 2 are determined as below.

$L\_ratio = $ left layer 1/left layer 2

$R\_ratio = $ right layer 1/right layer 2

Then, the ratio of the ratios of distortions of the left and right ROIs can be determined as below and displayed.

$comp = L\_ratio/L\_ratio$

According to this embodiment, the difference in the hardness of the tissue in corresponding regions, such as the left and right hands, feet, or breasts, can be quantitatively evaluated to increase the accuracy of a diagnosis.

Sixth Embodiment

Another embodiment of a diagnostic ultrasound system according to the present invention will be described with reference to FIGS. 14 and 15. As described above, the distortion of body tissue changes depending on the compression conditions. Thus, this embodiment provides an automatic pressurizing apparatus for applying compression to the body tissue at constant pressure and constant speed without depending on the repulsive force of the subject 1 so as to obtain a distortion elastic image with excellent reproducibility and evaluation ability.

Figure 14:
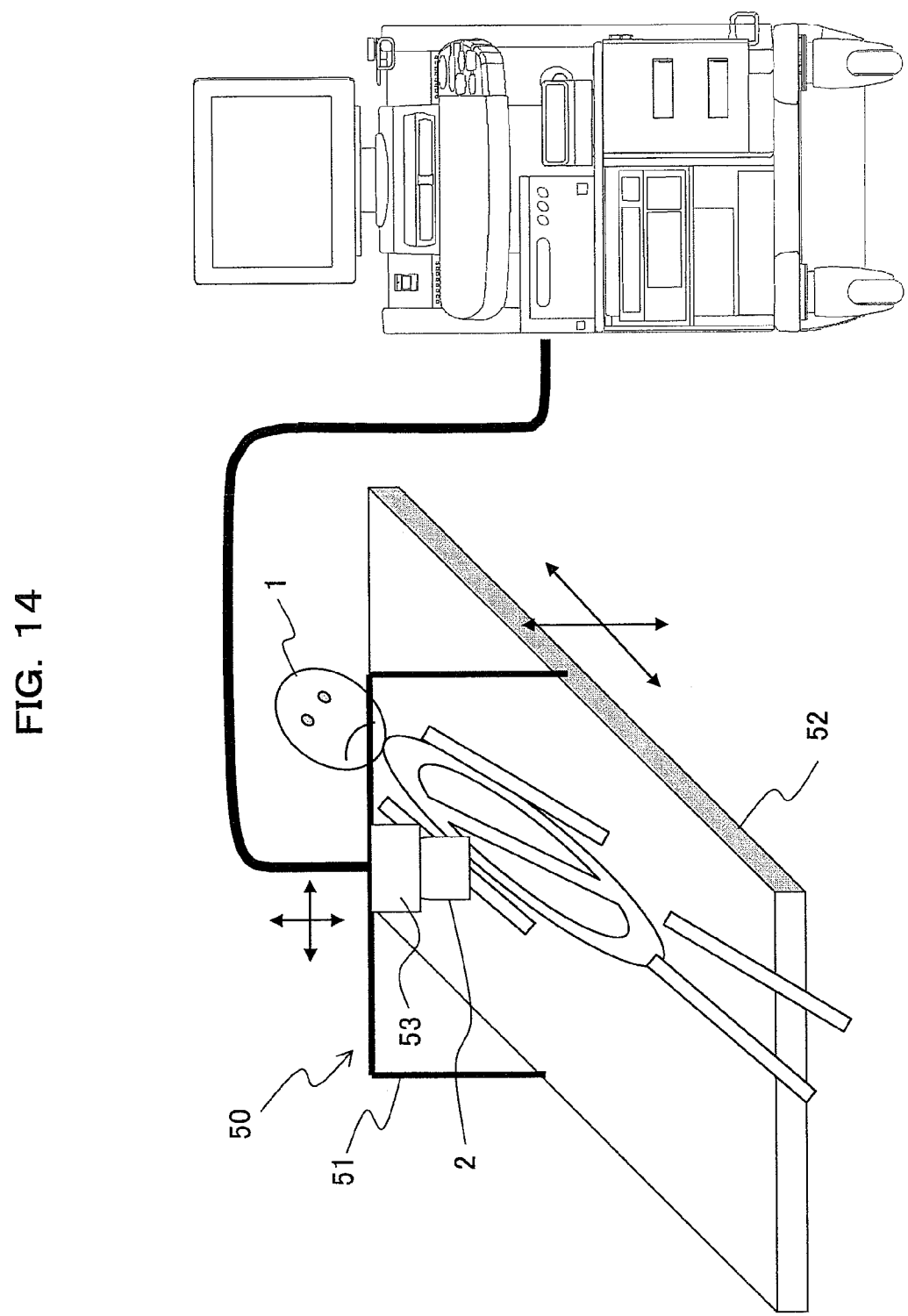
FIG. 14 illustrates an embodiment of an automatic pressurizing device of the diagnostic ultrasound system according to the present invention.

FIG. 14 illustrates an example of a pressurizing system 50 that is capable of increasing and decreasing the compression applied by the probe 2 to the subject 1. The pressurizing system 50 includes a bar 51 fixed to a bed 52 and a probe holding section 53 supported by the bar 51. The pressurizing system 50 enables the compression applied by the probe 2 to be increased or decreased by the examiner by operating one button, without touching the subject 1. In particular, the pressurizing system 50 takes into consideration the repulsive force from the subject 1. Accordingly, the probe 2 to be used for obtaining a tissue elastic image is fixed to the probe holding section 53, and the probe holding section 53 is repeatedly controlled to vertically move the probe 2 at constant speed and constant pressure by a stepping motor and the like in accordance with a control command.

Figure 15:
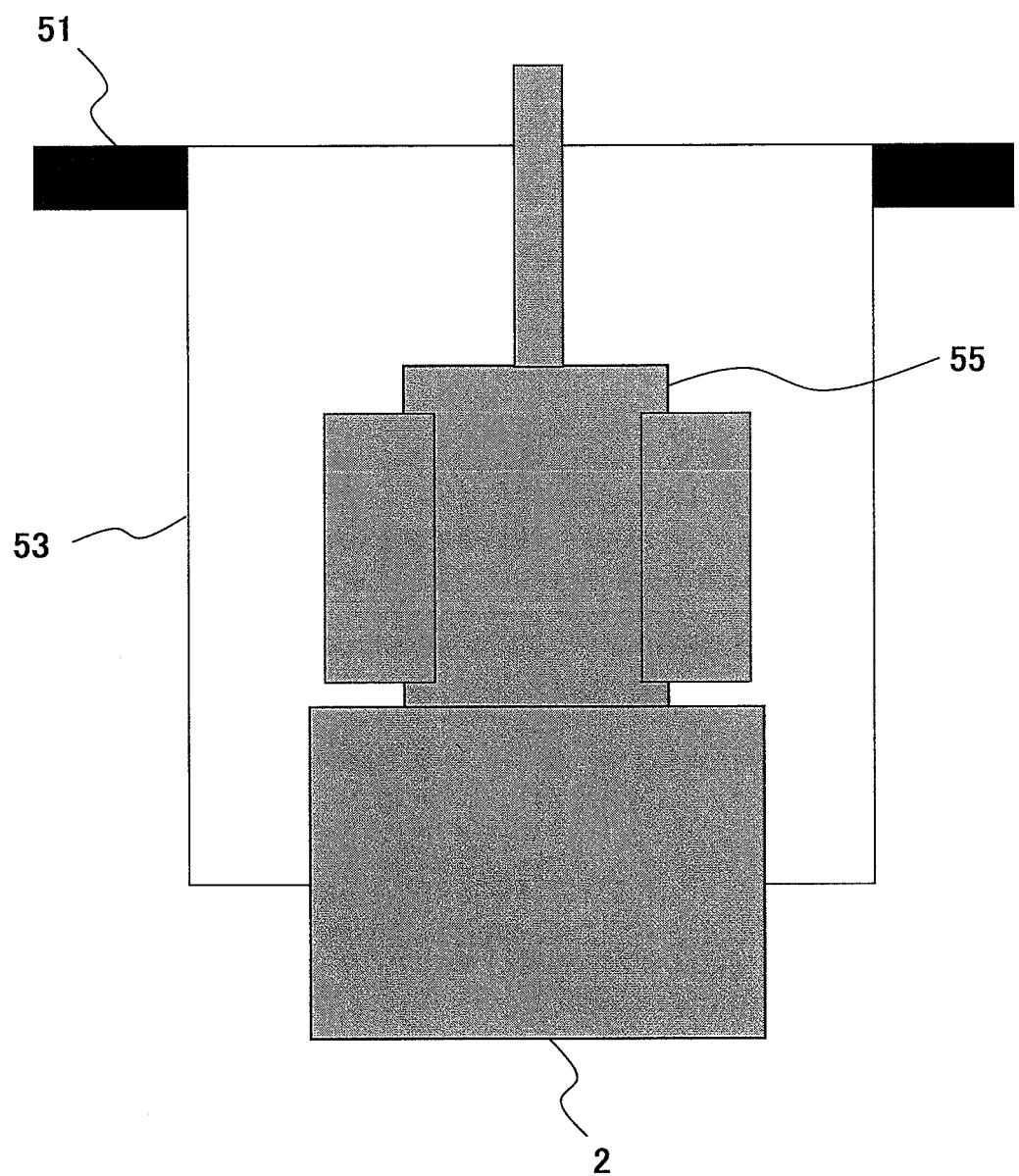
FIG. 15 illustrates the detailed structure of a pressurizing system for fixing the probe in FIG. 14.

FIG. 15 illustrates the concept of the structure of the probe holding section 53 holding the probe 2. As clearly shown in the drawing, the probe holding section 53 is fixed to the bar 51. The probe holding section 53 is provided with driving means 55, such as a stepping motor. The probe 2 is fixed to the driving means 55 with gripping means, such as a screw. The speed and pressure of the vertical movement of the probe 2 can be changed by range switching. In other words, the probe holding section 53 constitutes pressure controlling means, and the bar 51 constitutes fixing means for supporting the pressure controlling means.

The pressurizing system 50 having such a structure can be operated in conjunction with the diagnostic ultrasound system and can be switched at the diagnostic ultrasound system. Furthermore, the pressurizing system 50 can be programmed such that, after one command is issued, it continues to carry out vertical movement until a stop button is pushed or pressure is generated.

A conventionally proposed automatic pressurization system does not take into consideration the repulsive force from the subject 1. Therefore, when the body is hard, it receives a great repulsive force proportional to the hardness. Thus, the obtained numerical data was difficult to process.

In contrast, according to this embodiment, even when a repulsive force is received from the body of the subject 1, compression can be applied to the subject 1 at constant pressure and constant speed. Therefore, a tissue elastic image and its data having excellent reproducibility and evaluation ability can be obtained. As a result, for each region, the value of distortion obtained when pressure is applied at constant speed can be stabilized. Therefore, for example, the accuracy of differentiating benign and malignant cancer is improved.

In the above, the characteristics of a method of displaying an elastic image according to the present invention has been described while taking the distortion of tissue as an example. However, the present invention is not limited, to the distortion of tissue and an elasticity modulus may be used as a physical value correlating to the elasticity of the tissue.

The invention claimed is:

1. A diagnostic ultrasound system comprising:
an ultrasound probe;
an ultrasound cross-section data measuring unit configured to measure ultrasound cross-section data of a cross-section region of a subject with the ultrasound probe;
a signal processing unit configured to process the measured ultrasound cross-section data and generating a cross-sectional image;
an elastic-information computing unit configured to calculate an elastic information of tissue in the cross-section region on the basis of the measured ultrasound cross-section data and generating an elastic image of the cross-section region on the basis of the elastic information;
a display device for displaying the cross-sectional image and/or the elastic image;
an inputting unit configured to set a first region of interest set in a normal area of the subject in the elastic image displayed on the display device, and a second region of interest to be determined whether normal or not; and
an indexing unit configured to calculate a ratio of average values of the elastic information of the first region of interest and the second region of interest to presume hardness of the second region of interest,
the indexing unit is configured to calculate a ratio of the elastic information of the third region of interest and the sum of the elastic information of the first and the second regions of interest to compensate differences in magnitudes of compression forces.

2. The diagnostic ultrasound system according to claim 1, wherein the display device displays the ratio of average values of the elastic-information together with the cross-section image and/or elastic image.

3. The diagnostic ultrasound system according to claim 1, wherein
the display device is displayed a time phase bar for assigning the measurement time phase of the plurality of elastic images;
the elastic-information computing unit generates a plurality of the elastic images on the basis of a plurality of the ultrasound cross-section data sets measured in time sequence, and displays the elastic image corresponding to an assigned measurement time phase on the display device when a time phase bar is operated by the inputting unit.

4. The diagnostic ultrasound system according to claim 1, wherein the indexing unit displays a scale for a physical value of the display device and displays display marks at positions on the scale corresponding to the physical values of the first region of interest and the second region of interest.

5. The diagnostic ultrasound system according to claim 1, wherein the indexing unit calculates average value of the elastic-information of the regions of interest and relates to a minimum and a maximum value of the average values into a color to a lower limit value and an upper limit value of a dynamic range of color information for color conversion.

6. The diagnostic ultrasound system according to claim 1, the indexing unit variably sets the level of the dynamic range corresponding to an intermediate value when at least three regions of interest are set and the intermediate value is between the minimum value and the maximum value of the average value of the elastic-information.

7. The diagnostic ultrasound system according to claim 1, wherein the display device displays the change over time of the ratio of the elastic-information.

8. The diagnostic ultrasound system according to claim 1, wherein the indexing unit adds respectively the elastic-information of each region of interest over a plurality of frames and displays the change over the time of the added elastic-information on the display device.

9. The diagnostic ultrasound system according to claim 1, wherein the second region of interest is set in a large region surrounding the first region of interest.

10. The diagnostic ultrasound system according to claim 1, wherein the second region of interest is set away from the first region of interest.

11. The diagnostic ultrasound system according to claim 1, wherein the regions of interest include a third region of interest set in an affected area, and the first and the second regions of interest being set away from each other in the lateral direction of the elastic image and sandwiching third region of interest.

12. The diagnostic ultrasound system according to claim 1, wherein the first region of interest is set in a fat layer of the subject.

13. The diagnostic ultrasound system according to claim 1, wherein the first region is set in a region at a constant depth from a body surface of the subject.

14. The diagnostic ultrasound system according to claim 1, further comprising:
determining unit for determining whether or not the tissue in the region of interest is normal on the basis of the ratio of the elastic-information.

15. The diagnostic ultrasound system according to claim 1, wherein the indexing unit calculates another ratio of the basis of the two pair of ratio of the elastic-information calculated respectively with two pairs of the first and the second region of interests.

16. The diagnostic ultrasound system according to claim 1, further comprising:
pressuring controlling unit for supporting the ultrasound probe and for increasing or decreasing a compression applied to the subject with the ultrasound probe; and
fixing unit for supporting the pressuring controlling unit.

17. The diagnostic ultrasound system according to each one of claim 1, wherein the elastic-information is of a strain or an elastic modulus.

18. A diagnostic ultrasound system comprising:
an ultrasound probe;
ultrasound cross-section data measuring means for measuring ultrasound cross-section data of a cross-section region of a subject with the ultrasound probe;
signal processing means for processing the measured ultrasound cross-section data and generating a cross-sectional image;
elastic-information computing means for calculating an elastic information or an elastic modulus of tissue in the cross-section region on the basis of the measured ultrasound cross-section data and generating an elastic image of the cross-section region on the basis of the elastic information or the elastic modulus;
a display device for displaying the cross-sectional image and/or the elastic image;
inputting means for setting a first region of interest set in a normal area of the subject in the elastic image displayed on the display device, and a second region of interest to be determined whether normal or not; and
indexing means for calculating a ratio of average values of the elastic information or the elastic modulus of the first region of interest and the second region of interest to presume hardness of the second region of interest, the indexing means is configured to calculate a ratio of the elastic information of the third region of interest and the sum of the elastic information of the first and the second regions of interest to compensate differences in magnitudes of compression forces.

19. The diagnostic ultrasound system according to claim 1, wherein the first and second regions of interest are set in a frozen elastic image.

20. The diagnostic ultrasound system according to claim 1, wherein the display device displays the change over time of the strain ratio to represent an erroneous compression occurring when the elastic information changes over time.

* * * * *